United States Patent [19]

Mattalia

[11] 3,966,700

[45] June 29, 1976

[54] PROCESS FOR PREPARING SYNTHETIC L-PYROGLUTAMYL-L-HISTIDYL-L-PROLINAMIDE

[75] Inventor: Gabriele Mattalia, Rome, Italy

[73] Assignee: Istituto Farmacologico Serono, S.P.A., Rome, Italy

[22] Filed: Sept. 27, 1974

[21] Appl. No.: 509,843

[30] Foreign Application Priority Data
Oct. 19, 1973  Italy .................................. 53232/73

[52] U.S. Cl. ..................................... 260/112.5 TR
[51] Int. Cl.² .................. C07C 103/52; C07G 7/00
[58] Field of Search ........................... 260/112.5 TR

[56]       References Cited
       UNITED STATES PATENTS 3,753,969   8/1973   Folkers et al. .................... 260/112.5
3,757,003   9/1973   Folkers et al. .................... 260/112.5
3,816,387   6/1974   Cole et al. ....................... 260/112.5

OTHER PUBLICATIONS

Woolley: J. Am. Chem. Soc., 88, 2309–2310 (1966).
DuVigneaud et al.: J. Biol. Chem., 117, 27–36 (1937).

Primary Examiner—Lewis Gotts
Assistant Examiner—Reginald J. Suyat
Attorney, Agent, or Firm—Ostrolenk, Faber, Gerb & Soffen

[57]              ABSTRACT

Highly pure pyroglutamyl-histidyl-prolinamide is prepared by removing the protecting groups of the protected tripeptide by means of reductive deprotection with sodium in liquid ammonia followed by passing the crude deprotected tripeptide through a gel filtration means.

9 Claims, No Drawings

PROCESS FOR PREPARING SYNTHETIC L-PYROGLUTAMYL-L-HISTIDYL-L-PROLINAMIDE

Thyrotropin releasing hormone (TRH) or factor is the hypothalamic factor which stimulates the release of thyroid-stimulating hormone (thyrotropin) from the anterior lobe of pituitary.

TRH, first isolated from ovine hypothalami and then from porcine hypothalami, has been recently shown to have the structure of L-pyroglutamyl-L-hystidyl-L-prolinamide:

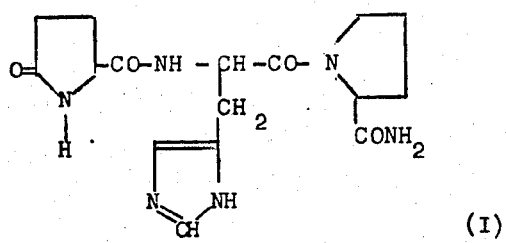

(I)

(hereinafter referred to as pGlu-His-Pro-NH$_2$) It has also been shown that synthetic TRH exhibits the same hormonal activities of the porcine TRH and that both porcine and synthetic TRH releases thyrotropin from the pituitary gland of normal men.

Accordingly, synthetic TRH is an useful tool to those who study the role of TRH as controlling factor in the normal and abnormal secretion of thyrotropin and the influence of TRH on the secretion of other pituitary hormones. Several procedures have been developed for preparing synthetic TRH. Most of them require the use of protected starting aminoacids and/or intermediate dipeptides and involve lengthy and tedious steps of removing the protecting groups.

On the other hand, when non-protected aminoacids are coupled with each other and with dipeptides, the yields are very low.

Considering that at least two theoretical coupling steps are required to prepare the desired tripeptide, an inadmissibly low ultimate yield based on the starting material results. There is also to be taken into consideration, in evaluating the overall economics of the process, that severe fractionation and purification steps are necessary to recover the desired intermediate and final products from the reaction mixtures inevitably containing substantial proportions of side products.

Therefore, the need exists of a new, speedy and economic process for the synthesis of highly pure TRH in high yields. According to the present invention highly pure synthetic TRH is produced in a high yield by first preparing the protected tripeptide, pyroglutamyl-N$^{im}$-benzyl-histidyl-prolinamide of the formula:

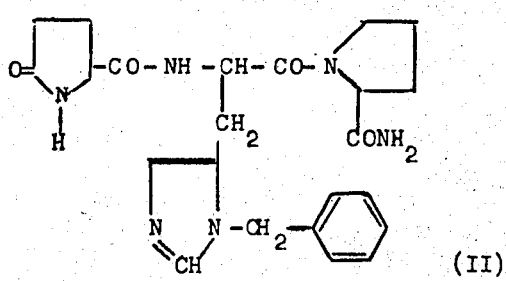

(II)

(hereinafter referred to as pGlu-(Bzl)His-Pro-NH$_2$), reductively deprotecting it by means of sodium in liquid ammonia, and then passing the resulting crude deprotected tripeptide through a gel-filtration means.

The protected tripeptide is preferably prepared in accordance with this invention by coupling N-t-butyloxycarbonyl-N$^{im}$-benzyl-histidine with prolinamide in the presence of N,N'-dicyclohexylcarbodiimide to give the protected dipeptide N-t-butyloxycarbonyl-N$^{im}$-benzyl-histidyl-prolinamide in a high yield.

Removal of t-butyloxy-carbonyl group by means of glacial acetic acid saturated with HBr affords N$^{im}$-benzyl-histidyl-prolinamide dihydrobromide which is purified by recrystallization and reacted with an active ester of pyroglutamic acid to give the protected tripeptide pGlu-(Bzl)His-Pro-NH$_2$. Alternatively, although less preferably, N-carbobenzoxy-pyroglutamic acid and the benzyl ester of N$^{im}$-benzyl-histidine are coupled by the mixed anhydride procedure and the resulting dipeptide ester is converted into pyroglutamyl-N$^{im}$-benzyl-histidine by selective hydrogenolysis. The protected dipeptide is then reacted with prolinamide in the presence of N,N'-dicyclohexylcarbodiimide to give pGlu-(Bzl)His-Pro-NH$_2$.

The reductive deprotection of the protected tripeptide in accordance with this invention is carried out by dissolving the tripeptide in liquid ammonia and then gradually adding sodium to the solution. The reaction time is counted starting from the moment when the solution assumes a persistent blue color. After an extremely short period ranging from thirty to 60 seconds, the reaction is quenched by carefully adding glacial acetic acid.

The reaction time is somewhat critical. Less than 30 seconds may be insufficient to achieve a substantially complete deprotection of the tripeptide. Periods longer than 60 seconds may lead to deterioration of the product.

The reduction by means of sodium in liquid ammonia is known to be a somewhat drastic method. As such, it had never been disclosed or suggested as a suitable route to deprotection of protected synthetic TRH. In sharp contrast with the above, according to this invention, the protected tripeptide pGlu-(Bzl)His-Pro-NH$_2$ undergoes the reductive deprotection step without any substantial decomposition or deterioration of the tripeptide molecule.

Another surprising feature of this invention is the great ease by which the deprotected tripeptide is chromatographically purified. A single passage of the deprotection reaction product through a chromatographic column packed with a suitable gel-filtration means directly gives a high yield of extremely pure synthetic TRH. The appropriate eluate fractions containing the desired product are easily recovered thanks to the sharp and symmetrical shape of the peak.

The final purification steps of the prior art procedures are lengthy and tedious in comparison with the single gel-filtration step in accordance with this invention.

This invention therefore provides a simple and straight-forward procedure which overcomes the main drawbacks of the prior art, that is, the problem of obtaining a non-deteriorated, substantially completely deprotected TRH, and the tediousness of the final purification of the product.

Illustrative examples of suitable gel-filtration media are polyacrylamide, dextrane and agarose gels. Such dextrane gels as, for example, those identified by the tradename SEPHADEX (a line of bead-formed dextrane gels produced by Pharmacia, Uppsala, Sweden) have been found perfectly suitable for carrying out the final purification step of the tripeptide in accordance with this invention.

Synthetic TRH is usually prepared from the L - forms of the starting aminoacids in order to match the structure of natural TRH. Accordingly, in the following examples and claims, the terms "pyroglutamic acid", "histidine" and "proline", their derivatives or their abbreviations are intended to mean the L - forms of the respective aminoacids or derivatives thereof.

However, it is within the scope of this invention to use either L or D or both forms.

The following Examples are illustrative of the present invention.

EXAMPLE 1

Prolinamide hydrochloride (6 g.) and N-t-butyloxycarbonyl-$N^{im}$-benzylhistidine (13.8 g.) were reacted in 200 ml. acetonitrile in the presence of 4.04 g. triethylamine and 10.3 g N,N'-dicyclohexylcarbodiimide to give N-t-butyloxycarbonyl-$N^{im}$-benzyl-histidyl-prolinamide as an oily residue. The oil was dissolved in 150 ml. of 2N hydrobromic acid solution in glacial acetic acid. The solution was kept at room temperature for 1 hour in a stoppered flask and then poured into 1500 ml. anhydrous ether. The solid precipitate was redissolved in methanol and precipitated again with ether to give 13.2 g (65.6%) of crystalline $N^{im}$-benzyl-histidyl-prolinamide dihydrobromide melting at 196–8°C after recrystallization from methanol-ether.

A suspension of 13.2 g. of the above protected dipeptide dihydrobromide in 150 ml. N,N-dimethylformamide containing 5.29 g. triethylamine was mixed with a solution of 9.9 g. pentachlorophenyl pyroglutamate in 130 ml. N,N-dimethylformamide. After being vigorously stirred at 0° to 5°C for 1 hour and then at room temperature for 24 hours, the reaction mixture was evaporated in vacuo to dryness.

The residue was dissolved in 100 ml. distilled water, the solution was filtered and the aqueous filtrate was evaporated again to dryness under high vacuum to give an oily residue which was redissolved in a mixture of 45 ml. ethyl acetate and 10 ml. methanol.

After filtering to remove the triethylamine hydrobromine precipitate, evaporating the filtrate to dryness in vacuo, washing the oily residue with 100 ml. anhydrous ether, filtering and drying, 8.24 g. (69.5%) crystalline pGlu-(Bzl) His-Pro-$NH_2$ were recovered.

The product gave a single spot ($R_f$=0.76) by TLC analysis on Silica Gel G using as eluent a 60:45:20 mixture of chloroform, methanol and 30% acetic acid.

EXAMPLE 2

3.1 g. N-carbobenzoxy-pyroglutamic acid were dissolved in 80 ml. tetrahydrofuran and to the solution was added 2 ml triethylamine and 1.27 ml. ethyl chloroformate under stirring. The reaction mixture was maintained at 0° C during the above additions and then at room temperature for 1 hour. A solution of 8 g. $N^{im}$-benzyl-histidine benzyl ester dibenzenesulfonate and 4 ml. triethylamine in 40 ml. tetrahydrofuran was then slowly added to the above mixture and reacted for about 4 hours.

After evaporating in vacuo until dry, washing the residue with 100 ml. water, extracting twice with 100 ml. methylene chloride, drying an anhydrous $Na_2SO_4$, filtering and evaporating to dryness in vacuo, the residue was dissolved in methanol and precipitated with anhydrous ether to give crystalline N-carbobenzoxy-pyroglutamyl-$N^{im}$-benzyl-histidine benzyl ester melting at 163–5°C - yield 4.2 g (61.4%).

4.2 g. of the above protected dipeptide were dissolved in 300 ml. ethanol, additioned with 0.5 g 10% palladium on carbon was added, and the material was hydrogenated for three hours at room temperature at a hydrogen pressure of 2 atmospheres. A yield of 2.19 g (85%) crystalline pyroglutamyl-$N^{im}$-benzyl-histidine was obtained by subjecting the hydrogenation reaction mixture to such usual operations as filtration, evaporation and precipitation with anhydrous ether from an ethanol solution of the residue (30 ml. ethanol were used to redissolve the residue).

2.19 g. pyroglutamyl-$N^{im}$-benzyl-histidine, 0.93 g. prolinamide hydrochloride and 2 ml. triethylamine were dissolved in 50 ml. N,N-dimethylformamide, cooled to 0°C and reacted with a solution of 1.52 g N,N'-dicyclohexylcarbodiimide in 20 ml. N,N-dimethylformamide.

After stirring for 48 hours at room temperature, filtering and evaporating to dryness, 1.25 g. (45%) pGlu-(Bzl)His-Pro-$NH_2$ were recovered and purified by recrystallization from methanol.

The product appeared to be identical by TLC analysis with that obtained according to Example 1 above.

EXAMPLE 3

A nitrogen-blanketed reactor equipped with magnetic stirrer was charged with about 500 ml. liquid ammonia and 1 g. pure pGlu-(Bzl)His-Pro-$NH_2$. Sodium was gradually added until the solution assumed a persistent blue color. After 30 seconds, the reaction was quenched by careful addition of about 1 ml. glacial acetic acid, the mixture was evaporated until dry and the residue was redissolved in 0.2 N acetic acid.

The resulting solution was filtered and passed through a 2.2 × 110 cm chromatographic column packed with Sephadex G-15 which had been equilibrated with 0.2 N acetic acid. The gel-filtration procedure carried out at 25 ml/hour using the same 0.2 N acetic acid as eluent gave a symmetrical eluate peak. The eluate fractions corresponding to the peak area were collected and lyophilized to afford 0.58 g (72.5%) highly pure pGlu-His-Pro-$NH_2$ (TRH). TLC analysis carried out on Silica Gel G plates (250 $\mu$) activated at 120°C for 1 hour using as eluent either the chloroform:methanol: conc. ammonia (60:45:20) system or the chloroform:methanol: 30% acetic acid (60:45:20) system showed a single spot in both cases at $R_f$ values of 0.6 and 0.36, respectively.

The product appeared to be completely free from ammonium (Nessler reagent test) and halide ions.

What is claimed is:

1. In a process for preparing highly pure pyroglutamyl-histidyl-prolinamide by synthesis from protected aminoacids, removal of the protecting groups, and final purification of the crude deprotected tripeptide, the improvement which comprises reductively deprotecting the protected tripeptide pyroglutamyl-$N^{im}$-benzyl-histidyl-prolinamide by contact thereof with sodium in liquid ammonia, and purifying the crude deprotected tripeptide by gel filtration.

2. The process of claim 1 wherein said reductive deprotection is carried out by dissolving the protected tripeptide in liquid ammonia, gradually adding sodium until the solution assumes a persistent blue color, and quenching the reaction with glacial acetic acid 30–60 seconds after the onset of the persistent blue color.

3. The process of claim 1 wherein the crude deprotected tripeptide is recovered from the reaction mixture and gel filtered without any intermediate purification step.

4. The process of claim 3 wherein the gel is dextrane gel.

5. The process of claim 4 wherein the crude deprotected tripeptide is purified by means of a single gel filtration step.

6. The process of claim 3 wherein the crude deprotected tripeptide is purified by means of a single gel filtration step.

7. The process of claim 1 wherein the crude deprotected tripeptide is purified by means of a single gel filtration step.

8. The process of claim 2 wherein the gel is dextrane gel.

9. The process of claim 8 wherein the crude deprotected tripeptide is purified by means of a single gel filtration step.

* * * * *